April 24, 1934. A. MONTGOMERY Plant Pat. 95
HYBRID TEA ROSE
Filed Aug. 1, 1933
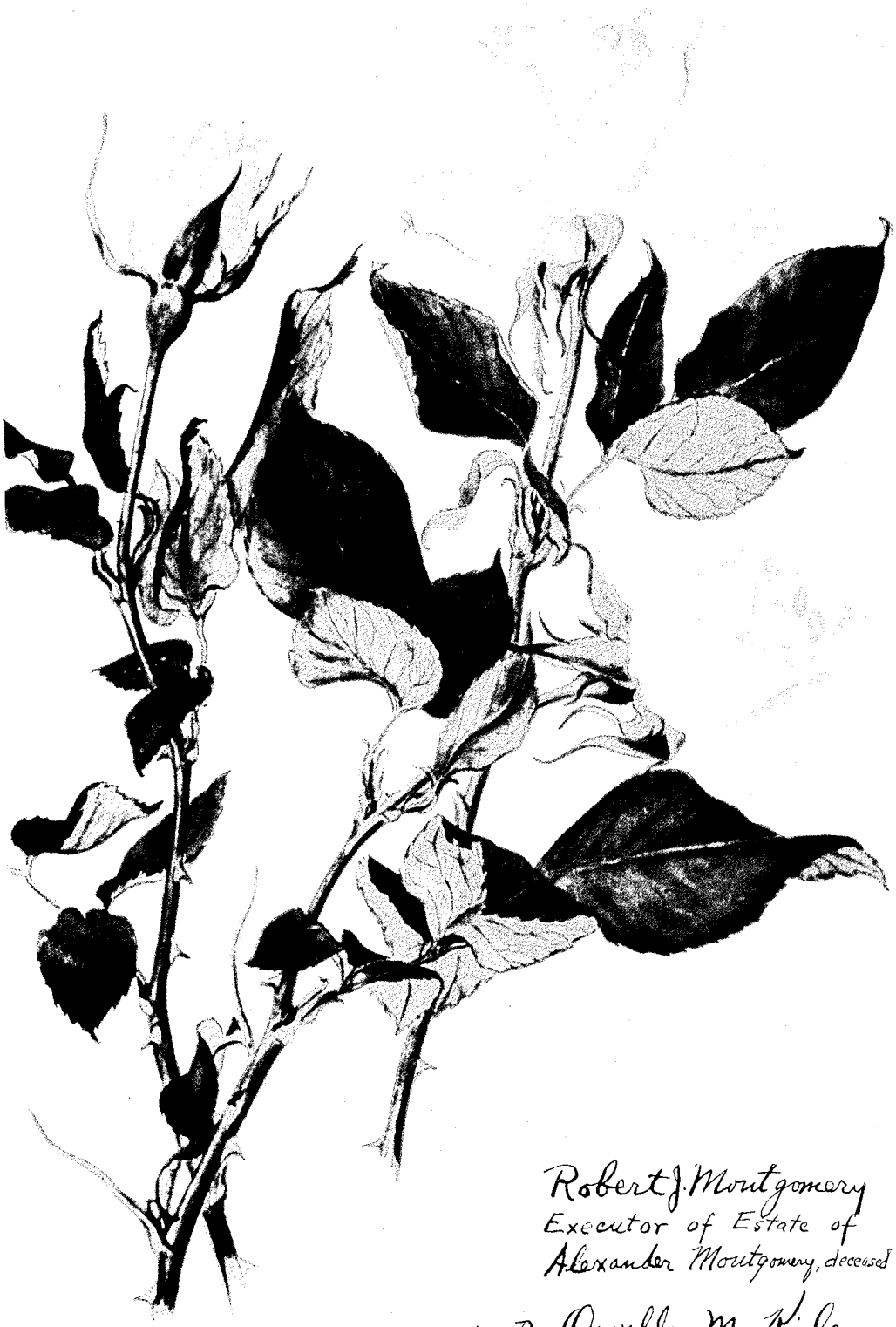
Robert J. Montgomery
Executor of Estate of
Alexander Montgomery, deceased
By Orville M Kile
PLANT PATENT AGENT Patented Apr. 24, 1934 Plant Pat. 95

UNITED STATES PATENT OFFICE

95

HYBRID TEA ROSE

Alexander Montgomery, deceased, late of Amherst, Mass., by Robert J. Montgomery, executor, Amherst, Mass., assignor to The Montgomery Company, Incorporated, Hadley, Mass.

Application August 1, 1933, Serial No. 683,222

1 Claim. (Cl. 47—61)

This invention relates to improvements in hybrid tea roses designed both for commercial hothouse culture and for out-door ornamental use. The principal improvement lies in the distinctive "orange-buff" to "peach red" color, but there are other notable points of distinction.

This new variety is the result of careful, painstaking plant breeding work. It is the offspring of a cross between the variety "Madame Butterfly" and the variety "Premier Supreme," Madame Butterfly being the female parent. The first plant of this new variety came into blossom in April 1929, when its superior qualities were recognized. A sexual propagation was begun shortly thereafter.

The accompanying illustrations show in full color and, in the original, approximately full size, a closed bud, a partially opened bud and an open flower of this variety, together with foliage and stems—all depicted as nearly as possible in their true forms and colors.

The following is a detailed description:

The bush or plant is of medium size, being about the height of a typical Joanna Hill plant grown under similar conditions, but being more bushy because of the larger number of branches thrown out from the bottom and sides.

On account of the large number of bottom and side shoots, the lack of blind wood, and the tendency to "come back" quickly after cutting, this variety is a heavy producer comparing favorably with the best hybrid teas in this respect.

*Disease resistance.*—This variety is particularly resistant to black spot and mildew. When grown in the same greenhouse with Joanna Hill the superior resistance of this new variety is readily noticeable. The foliage retains its healthy green appearance even when other varieties become yellow and streaked.

This variety reproduces readily and does not require the careful cultural attention necessary to the growth of many hybrid tea varieties.

Foliage is light green, vigorous in appearance, and plentiful. Leaves are medium in size with finely toothed edges. The leaves have a tendency to curl and crinkle rather than to lie flat. The first leaves below the flower occur as a pair, arising at approximately the same point on opposite sides of the stem—an unusual arrangement.

*Stem.*—Medium in size, peduncle short with leaves occurring within 2½ to 3 inches of the flower. Short, thin spines are found on the peduncle and thorns below the first leaves. The thorns are numerous and light in color.

No thorns or spines are found on the petioles of the leaves.

Stipules are broad and terminate in sharp points, disposed at an angle though not curling.

*Sepals.*—Five in number, broad at base and terminating in rather sharp points, not foliaceous in character although three of the five are branched while the remaining two are regular in form.

Hips rather prominent.

Buds are somewhat urn-shaped in form when beginning to open.

*Flowers.*—As the rose bud opens the outer row of petals is "orange-buff" to "Capucine-orange" (Plate III, Ridgway's Color Standard and Nomenclature). All the central portion of the flower is "peach red" (Plate I, Ridgway's Color Standard and Nomenclature).

After the outer row of petals opens fully and curls back the remaining petals ordinarily open slowly, so that for fully two days the rose has the appearance of an erect nearly-closed center arising from a background of lighter colored curled (4 to 6) petals.

Each petal has at its base a considerable area of "light cadmium yellow" (Plate IV, Ridgway's Color Standard and Nomenclature). A slight edging of this same color is found on many of the petals for a distance of a half inch or more from the base. Also a narrow, broken, yellowish line is found running up the middle of the back side of many of the petals, particularly those in the central part of the flower.

The yellowish tones are scarcely noticeable on the opening flower but become more prominent as the outer row of petals opens completely and curls back.

As the central petals age and open out, the peach red color diffuses somewhat and the color effect becomes "salmon-orange" (Plate II, Ridgway's Color Standard and Nomenclature).

It is a notable fact that these distinctive orange tones vary little with the season. They are maintained despite cloudy weather.

The flower ranks as medium in size. In the latter part of May it has 20 to 22 petals.

The large number of stamens found in this flower are mounted on buff-colored anthers of medium size. The moderate number of reddish pistils are capped by whitish tops.

The odor is moderately fragrant.

Having thus disclosed this invention, what is claimed as new is:

The variety of hybrid tea rose herein shown and described, characterized particularly by the distinctive buff-orange color of its flowers, its vigorous and profuse foliage of light green color, its superior growing and reproduction habits and its resistance to diseases.

ROBERT J. MONTGOMERY,
*Executor of the Estate of Alexander Montgomery, Deceased.*